(12) United States Patent
Baker et al.

(10) Patent No.: US 10,502,054 B2
(45) Date of Patent: Dec. 10, 2019

(54) FLUID PROPERTIES MEASUREMENT USING CHOKE VALVE SYSTEM

(71) Applicant: OneSubsea IP UK Limited, London (GB)

(72) Inventors: Andrew C. Baker, Bergen (NO); Lars Noekleberg, Bergen (NO); Harald Solheim, Bergen (NO)

(73) Assignee: OneSubsea IP UK Limited, London (GB)

(*) Notice: Subject to any disclaimer, the term of this patent is extended or adjusted under 35 U.S.C. 154(b) by 79 days.

(21) Appl. No.: 15/791,996

(22) Filed: Oct. 24, 2017

(65) Prior Publication Data

US 2019/0120050 A1 Apr. 25, 2019

(51) Int. Cl.

| | |
|---|---|
| *E21B 34/00* | (2006.01) |
| *E21B 49/08* | (2006.01) |
| *G01N 33/18* | (2006.01) |
| *G01V 11/00* | (2006.01) |
| *E21B 43/36* | (2006.01) |
| *E21B 41/00* | (2006.01) |
| *E21B 43/12* | (2006.01) |
| *E21B 47/00* | (2012.01) |

(Continued)

(52) U.S. Cl.
CPC .............. *E21B 49/08* (2013.01); *E21B 34/00* (2013.01); *E21B 41/0007* (2013.01); *E21B 43/12* (2013.01); *E21B 43/36* (2013.01); *E21B 47/0001* (2013.01); *E21B 47/01* (2013.01); *G01N 33/18* (2013.01); *G01V 11/002* (2013.01); *E21B 34/04* (2013.01); *E21B 2049/085* (2013.01)

(58) Field of Classification Search
CPC ...... E21B 49/08; E21B 34/00; E21B 41/0007; E21B 43/12; E21B 43/36; E21B 47/0001; E21B 47/01; E21B 34/04; E21B 2049/085; G01N 33/18; G01V 11/002
See application file for complete search history.

(56) References Cited

U.S. PATENT DOCUMENTS

| | | | | |
|---|---|---|---|---|
| 3,368,587 | A * | 2/1968 | Wells | E21B 43/12 138/44 |
| 7,152,682 | B2 * | 12/2006 | Hopper | B01D 17/0217 166/357 |

(Continued)

OTHER PUBLICATIONS

Extended European Search Report issued in European Patent Appl. No. 18201489.4 dated Mar. 25, 2019; 10 pages.

*Primary Examiner* — Yong-Suk Ro
(74) *Attorney, Agent, or Firm* — Brandon S. Clark

(57) ABSTRACT

A technique facilitates monitoring of a multiphase fluid flow. The fluid flow is directed through a choke valve comprising a choke actuation system which controls a flow rate of the fluid passing through the choke valve. The choke valve also comprises a velocity reduction area which is created by a choke gallery. The choke gallery reduces the velocity of the fluid flow to encourage separation of phases of the multiphase fluid. A sensor is positioned along the gallery at a desired region to monitor a property of at least one separated phase of the multiphase fluid. For example, the sensor may be positioned proximate a bottom of the choke gallery to monitor a property related to a water phase which separates and transitions to the bottom due to its greater density.

20 Claims, 2 Drawing Sheets

(51) Int. Cl.
*E21B 47/01* (2012.01)
*E21B 34/04* (2006.01)

(56) References Cited

U.S. PATENT DOCUMENTS

| | | | | |
|---|---|---|---|---|
| 8,460,438 | B2* | 6/2013 | Meek | B01D 17/0217 |
| | | | | 95/243 |
| 2006/0061515 | A1* | 3/2006 | Posluszny | H01Q 1/243 |
| | | | | 343/803 |
| 2009/0139345 | A1* | 6/2009 | Xie | G01F 15/02 |
| | | | | 73/861.04 |
| 2010/0031754 | A1* | 2/2010 | Atkinson | G01N 1/14 |
| | | | | 73/861.04 |
| 2010/0059221 | A1 | 3/2010 | Vannuffelen et al. | |
| 2010/0300696 | A1 | 12/2010 | McCalvin et al. | |
| 2011/0100710 | A1* | 5/2011 | Fossli | E21B 21/001 |
| | | | | 175/7 |
| 2011/0240298 | A1 | 10/2011 | Rota et al. | |
| 2013/0025874 | A1* | 1/2013 | Saunders | E21B 49/08 |
| | | | | 166/357 |
| 2015/0275613 | A1 | 10/2015 | Minnock et al. | |
| 2016/0186869 | A1* | 6/2016 | Hopper | E21B 34/02 |
| 2018/0073901 | A1* | 3/2018 | Hopper | G01F 1/40 |
| 2018/0093203 | A1* | 4/2018 | Husveg | B01D 17/02 |

\* cited by examiner

FLUID PROPERTIES MEASUREMENT USING CHOKE VALVE SYSTEM

BACKGROUND

In many types of subsea production operations, hydrocarbon fluids and/or other process fluids are flowed through process flow lines. The flowing process fluids may be multiphase fluids containing various types of liquid and gas phases. For example, a process fluid may contain a gas-oil-water mixture. Additionally, the water phase may contain salt water and mixtures of water and water soluble chemicals. However, determining properties related to individual constituents of the multiphase fluids can be difficult while the phases remain mixed.

SUMMARY

In general, a system and methodology are provided for monitoring a fluid flow of, for example, a multiphase fluid. The fluid flow is directed through a choke valve which may be positioned along, for example, a process fluid flow line. The choke valve comprises a choke actuation system which controls a flow rate of the fluid passing through the choke valve. Additionally, the choke valve comprises a velocity reduction area which is created by a gallery of the choke valve. The choke gallery reduces the velocity of the fluid flow to encourage separation of phases of the multiphase fluid. A sensor is positioned along the gallery at a desired region to monitor a property of at least one separated phase of the multiphase fluid. For example, the sensor may be positioned proximate a bottom of the choke gallery to monitor a water phase which separates and transitions to the bottom due to its greater density.

However, many modifications are possible without materially departing from the teachings of this disclosure. Accordingly, such modifications are intended to be included within the scope of this disclosure as defined in the claims.

BRIEF DESCRIPTION OF THE DRAWINGS

Certain embodiments of the disclosure will hereafter be described with reference to the accompanying drawings, wherein like reference numerals denote like elements. It should be understood, however, that the accompanying figures illustrate the various implementations described herein and are not meant to limit the scope of various technologies described herein, and.

DETAILED DESCRIPTION

Figure 1:
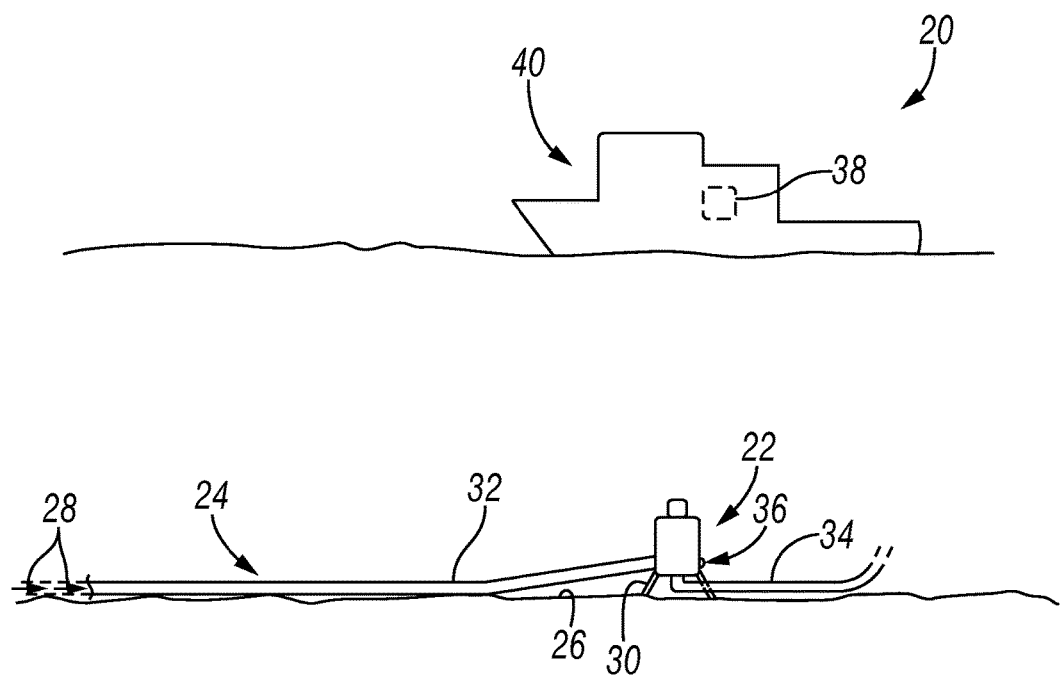
FIG. 1 is a schematic illustration of an example of a subsea system having a choke valve positioned along a process fluid flow line, according to an embodiment of the disclosure.

In the following description, numerous details are set forth to provide an understanding of some embodiments of the present disclosure. However, it will be understood by those of ordinary skill in the art that the system and/or methodology may be practiced without these details and that numerous variations or modifications from the described embodiments may be possible.

The present disclosure generally relates to a system and methodology which facilitate monitoring of a fluid flow, e.g. a multiphase fluid flow. In a variety of applications, the fluid flow is a subsea fluid flow which may comprise a multiphase flow of a gas-oil-water mixture. However, the system and methodology may be used to monitor a variety of other types of fluid flows in other environments, including surface environments.

According to an embodiment, the fluid flow is directed through a choke valve which may be positioned along, for example, a process fluid flow line. The choke valve comprises a choke actuation system which controls a flow rate of the fluid passing through the choke valve. By way of example, the choke actuation system may comprise a cylindrical structure having flow passages, e.g. perforations, through which the fluid is able to flow. The fluid flow rate through the flow passages may be controlled via a slide member, e.g. a piston or a sleeve, slidably mounted along the cylinder. By way of example, the slide member may be moved via an actuator between a fully open flow position and a no flow position.

Additionally, the choke valve may comprise a velocity reduction area which is created by a gallery of the choke valve. The choke gallery establishes an expanded flow region which reduces the velocity of the fluid flow to encourage separation of phases of the multiphase fluid. A sensor system may be positioned along the choke gallery at a desired region to monitor a property related to at least one separated phase of the multiphase fluid. For example, the sensor system may comprise a sensor positioned proximate a bottom of the choke gallery to monitor for a property related to a heavier phase, e.g. a water phase, which separates and transitions to the bottom due to its greater density.

Depending on the application, the sensor system may be an individual sensor selected to monitor a parameter such as salinity or conductivity. However, the sensor system also may be in the form of a plurality of sensors of the same type or dissimilar types for measuring a single property or a plurality of properties at desired locations along the choke gallery. The sensor or sensors output data related to the property(ies) to a suitable processing system which is then able to process the data to determine the presence and/or characteristics of the multiphase fluid flowing through the choke valve and associated flow line.

According to one operational example, the choke valve is a subsea choke valve having a perforated cylinder to create flow passages which can be progressively blocked with, for example, an internal piston or an external sleeve driven by an actuator. The choke valve may be operated to control the flow rate of a multiphase fluid in a subsea process line. The inlet section to the choke valve may be coupled to a choke gallery which surrounds the perforated cylinder. The choke gallery effectively creates an increased area, e.g. a larger cross-sectional area relative to the cross-sectional area of the subsea process line, so as to reduce multiphase fluid velocities. The reduced velocity of the fluid flow in the choke gallery allows the heavier phase, e.g. the higher density water phase, to at least partially separate. In this example, the heavier water phase tends to settle to a bottom of the choke gallery. Sensors may be placed along the bottom of the choke gallery to detect and monitor the water phase and/or other heavier phases. In some embodiments, the configuration of the choke gallery may be selected to optimize accumulation of liquid.

Referring generally to FIG. 1, an example of a subsea system 20 is illustrated as having a choke valve 22 positioned along a flow line 24, e.g. a subsea process fluid line. Depending on the embodiment, the subsea system 20 may comprise many types of subsea installations, e.g. wellheads, Christmas trees, manifolds, positioned at various locations to facilitate production of hydrocarbon fluids. In this example, the hydrocarbon fluids may be referred to as process fluids which flow through flow line 24 as well as other flow lines that may be positioned along, for example, a sea floor 26. The process fluids, e.g. multiphase process fluids, are indicated by arrows 28.

The choke valve 22 is illustrated as a standalone unit mounted on a support structure 30, but the choke valve 22 may be part of various other subsea installations located along the sea floor 26. Additionally, the choke valve 22 is illustrated as a relatively large structure but the actual choke valve 22 may be relatively smaller and, in some embodiments, integrated into or coupled with other subsea components. It should also be noted the choke valve 22 may be positioned along flow lines 24 used for flowing other types of process fluids at subsea locations or surface locations.

In the illustrated example, a first section 32 of flow line 24 is illustrated as coupled to an inlet side of choke valve 22 and a second section 34 of flow line 24 is illustrated as coupled to an outlet side of choke valve 22. The flow line 24 may be routed to other subsea installations, to a surface facility, or to another desired location. In some applications, the flow line 24 may be routed at least partially along the surface.

As described in greater detail below, the choke valve 22 is constructed to facilitate separation of phases in the multiphase fluid 28. By way of example, the separation of phases may comprise at least partial separation of a water phase from oil and gas phases in a multiphase hydrocarbon fluid. A sensor system 36 collects data on one or more of the phases for analysis on a processing system 38.

By way of example, the processing system 38 may be located on a surface facility 40, e.g. a surface vessel, or at another suitable subsea location, surface location, and/or land-based location. The data from sensor system 36 may be provided to processing system 38 via a variety of techniques, including wireless or wired transmission of data from the subsea location to the surface location. In some embodiments, the sensor data may be stored subsea and later retrieved to the surface. Subsea vehicles, e.g. remotely operated vehicles (ROVs) or autonomous underwater vehicles (AUVs), also may be used to retrieve the data and/or to couple umbilicals with the sensor system 36 to enable transmission of data to the processing system 38.

The processing system 38, in turn, may be used to determine various characteristics of the process fluid flowing through the corresponding flow line 24. For example, salinity sensors, conductivity sensors, and/or other sensors may be used to detect and monitor characteristics of a separated phase, such as a separated water phase. This data may then be provided to processing system 38 for further analysis.

Figure 2:
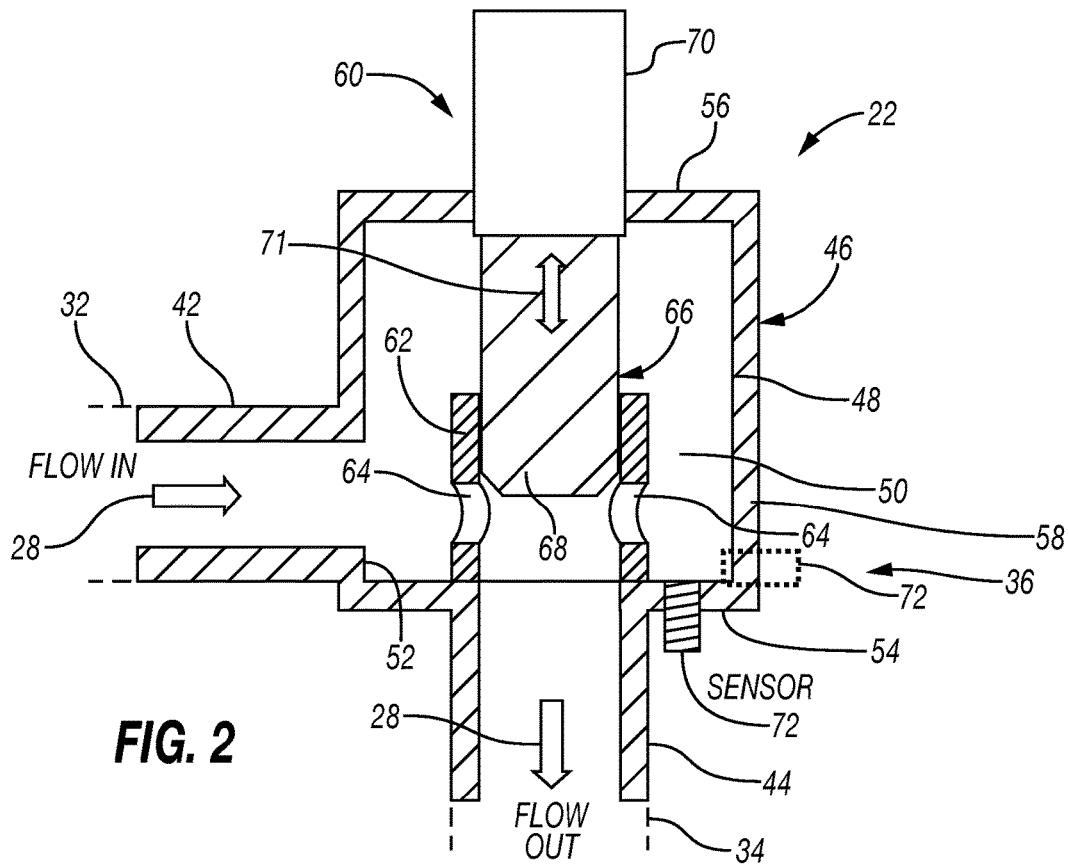
FIG. 2 is a schematic cross-sectional illustration of an example of a choke valve, according to an embodiment of the disclosure.

Referring generally to FIG. 2, an example of choke valve 22 is illustrated. In this embodiment, the choke valve 22 comprises an inlet section 42 coupled with first section 32 of flow line 24 and an outlet section 44 coupled with second section 34 of flow line 24. The illustrated choke valve 22 also comprises a choke gallery 46 coupled to the inlet section 42 and the outlet section 44.

The choke gallery 46 may be formed via a valve housing 48 to create an internal fluid flow region 50 in fluid communication with inlet section 42 and outlet section 44. The flow region 50 is larger than the flow area of flow line 24 and this larger region creates a velocity reduction as the multiphase fluid 28 flows from the process flow line 24 and into the choke gallery 46. For example, the choke gallery 46 may have a larger cross-sectional flow area than the cross-sectional flow area of the corresponding flow line 24.

The larger cross-sectional flow area of the choke gallery 46 causes a heavier phase of the multiphase fluid 28 to separate, e.g. at least partially separate, and settle to a bottom 52 of the choke gallery 46. The separation results from the reduction in flow velocity experienced by the multiphase fluid 28 as it moves into the flow region 50 of choke gallery 46. The settling of the heavier phase to bottom 52 results from gravity acting on the heavier phase of the multiphase fluid 28.

The choke gallery 46 may have various configurations. In the illustrated embodiment, however, the choke gallery 46 is formed via valve housing 48 and may be generally cylindrical having a bottom wall 54, a top wall 56, and a cylindrical sidewall 58 extending from the bottom wall 54 to the top wall 56 (see also FIG. 3). In some embodiments, the inlet section 42 and the outlet section 44 also may be generally cylindrical and oriented for coupling with the corresponding sections 32, 34 of flow line 24.

According to the embodiment illustrated, the subsea choke valve 22 also comprises a choke actuator system 60 disposed in the choke gallery 46, e.g. extending at least partially into the internal flow region 50 of choke gallery 46. The choke actuator system 60 is adjustable to control a flow rate of the multiphase fluid 28 through the subsea flow line 24, e.g. through a subsea process flow line. By way of example, the choke actuator system 60 may comprise a cylinder 62 having flow passages 64 through which the multiphase fluid is able to flow from inlet section 42 to outlet section 44.

Additionally, the choke actuator system 60 may comprise a slide member 66 slidably mounted along the cylinder 62 for movement with respect to flow passages 64. In other words, the slide member 66 may be moved so as to allow, block, or partially block flow through the flow passages 64, thus enabling control over the flow rate of multiphase fluid 28 through the subsea choke valve 22. In some embodiments, the slide member 66 may be in the form of a piston 68, as illustrated, but the slide member 66 may have other configurations, e.g. a slidable sleeve which may be shifted to desired flow positions with respect to flow passages 64.

The slide member 66 may be selectively moved via an actuator 70 coupled to the slide member 66. The actuator 70 enables controlled movement of the slide member 66 to different positions for controlling the amount/rate of fluid flow through the flow passages 64. Depending on the application and environment, the actuator 70 may have a variety of forms such as a hydraulic actuator, electric actuator, or other suitable actuator for moving slide member 66 to desired flow positions.

Figure 3:
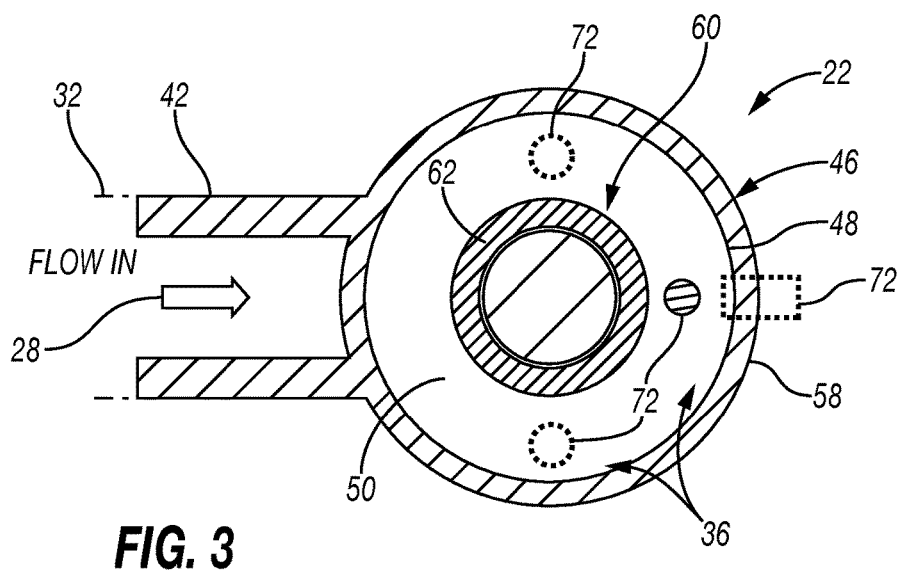
FIG. 3 is a schematic top view of the choke valve illustrated in FIG. 2, according to an embodiment of the disclosure.

Referring again to FIGS. 2 and 3, the choke valve 22 also may comprise sensor system 36 having a sensor 72, e.g. a plurality of sensors 72. The sensor(s) 72 may be positioned at the bottom 52 of the choke gallery 46 to measure a property of the heavier phase which settles to the bottom 52. By way of example, at least one sensor 72 may be mounted through the bottom wall 54. In some embodiments, a plurality of sensors 72 may be mounted through bottom wall 54, as illustrated in FIG. 3, to monitor one or more properties of the fluid disposed in bottom 52.

However, the sensor or sensors 72 also may be mounted to extend through the cylindrical sidewall 58 as indicated by dashed lines in FIG. 2. Sensors 72 also may be mounted in both the bottom wall 54 and cylindrical wall 58 as well as other suitable locations for monitoring desired fluid properties, e.g. properties related to fluid presence and/or fluid characteristics.

By way of example, the sensor or sensor 72 may comprise salinity sensors, conductivity sensors, or other sensors to determine the presence and/or characteristics of fluid in bottom 52 of choke gallery 46. In a variety of applications, for example, the multiphase fluid 28 may comprise water which is a heavier phase that tends to settle to bottom 52 of choke gallery 46. By using salinity sensors, conductivity sensors, or other suitable sensors 72, the presence of water (or other phases) may be detected and monitored. Various other types of sensors 72 also may be used to monitor desired properties related to fluid in choke gallery 46.

An available sensor 72 which may be used individually or in groups to monitor multiphase fluids is the AquaWatcher™ sensor available from OneSubsea, a Schlumberger company. The AquaWatcher™ sensor may be used to measure electrical properties of the water phase and aqueous solutions in multiphase flow, e.g. gas-oil-water flow. The water phase may comprise saltwater and/or mixtures of water and water soluble chemicals such as ethylene glycol. As described above with respect to generic sensors 72, the AquaWatcher™ sensor(s) 72 may be located along the bottom 52 of the choke gallery 46 (see sensors 72 illustrated in FIGS. 2 and 3). When the multiphase fluid 28 moves into the choke gallery 46, the flow velocity decreases so the water phase at least partially separates from the oil and gas phases. Because the water phase has a higher density than the oil and gas phases, the water phase tends to accumulate at the bottom 52 which enables monitoring of the water phase via the AquaWatcher™ sensor(s) 72.

Depending on the parameters of a given operation, the subsea system 20 for monitoring fluid flow may be used with many types of devices and systems. For example, the subsea choke valve 22 may be used with many types of subsea installations, pipelines, flow control systems, and subsea components to facilitate monitoring of a fluid flowing therethrough. The choke valve 22 may utilize various types of actuation systems 60 as well as various types of sensor systems 36 incorporating one or more types of sensors 72.

For example, sensors 72 may be utilized for monitoring various properties related to the overall multiphase fluid 28 as well as for monitoring properties with respect to individual phases. Sensors 72 may be used for monitoring properties of the heavier phase and/or lighter phases. Additionally, the choke gallery 46 may have various sizes and configurations and may be constructed to provide desired velocity decreases as the multiphase fluid 28 flows through the choke valve 22.

Although a few embodiments of the disclosure have been described in detail above, those of ordinary skill in the art will readily appreciate that many modifications are possible without materially departing from the teachings of this disclosure. Accordingly, such modifications are intended to be included within the scope of this disclosure as defined in the claims.

What is claimed is:

1. A system for monitoring a fluid flow, comprising:
a subsea process line for flowing a multiphase fluid;
a subsea choke valve positioned along the subsea process line, the subsea choke valve having:
an inlet section;
a choke gallery coupled to the inlet section and having a larger cross-sectional flow area than the subsea process line;
an outlet section coupled to the choke gallery; and
a choke actuator system disposed in the choke gallery, the choke actuator system being adjustable to control a flow rate of the multiphase fluid through the subsea process line, the larger cross-sectional area of the choke gallery causing a reduction in flow velocity enabling a heavier phase of the multiphase fluid to separate and transition to a bottom of the choke gallery; and
a sensor positioned at the bottom of the choke gallery to measure a property of the heavier phase.

2. The system as recited in claim 1, wherein the inlet section is generally cylindrical and oriented for coupling with a first section of the subsea process line; and the outlet section is generally cylindrical and oriented for coupling with a second section of the subsea process line.

3. The system as recited in claim 1, wherein the choke gallery comprises a cylindrical housing having a bottom wall, a top wall, and a cylindrical side wall extending from the bottom wall to the top wall.

4. The system as recited in claim 3, wherein the sensor extends through the bottom wall.

5. The system as recited in claim 3, wherein the sensor extends through the cylindrical sidewall proximate the bottom wall.

6. The system as recited in claim 1, wherein the sensor comprises a plurality of sensors.

7. The system as recited in claim 1, wherein the sensor comprises a salinity sensor.

8. The system as recited in claim 1, wherein the sensor comprises a conductivity sensor.

9. The system as recited in claim 1, wherein the choke actuator system comprises:
a cylinder having flow passages through which the multiphase fluid is able to flow;
a slide member slidably mounted along the cylinder; and
an actuator coupled to the slide member to move the slide member to different positions, the different positions controlling the amount of fluid flow through the flow passages and thus from the inlet section to the outlet section.

10. The system as recited in claim 9, wherein the slide member is a piston.

11. A system, comprising:
a choke valve having: an inlet section and an outlet section through which a process fluid is received and discharged, respectively; a choke gallery enlarged to slow the velocity of the process fluid between the inlet section and the outlet section to enable phase separation; a choke actuation system adjustable to control flow rate of the process fluid through the outlet section; and a sensor positioned at a bottom of the choke gallery to measure a fluid property of a fluid phase disposed along a bottom of the choke gallery.

12. The system as recited in claim 11, further comprising a subsea process line for flowing the process fluid, the choke valve being coupled into the subsea process line.

13. The system as recited in claim 11, wherein the choke gallery comprises a cylindrical housing having a bottom wall, a top wall, and a cylindrical side wall extending from the bottom wall to the top wall.

14. The system as recited in claim 13, wherein the sensor extends through the bottom wall.

15. The system as recited in claim 13, wherein the sensor extends through the cylindrical side wall proximate the bottom wall.

16. The system as recited in claim 11, wherein the choke actuation system comprises a cylinder having flow passages through which the process fluid is able to flow at a rate determined by a slide member slidably mounted along the cylinder.

17. The system as recited in claim 16, wherein the choke actuation system further comprises an actuator coupled to the slide member to move the slide member to different positions so as to control the amount of process fluid flowing through the flow passages.

18. A method, comprising:
 positioning a choke valve along a process line;
 delivering a multiphase fluid through the process line;
 controlling a flow rate of the multiphase fluid with a choke actuation system of the choke valve;
 creating a velocity reduction in a gallery of the choke valve to encourage separation of phases of the multiphase fluid; and
 using a sensor positioned along the gallery to monitor a property of at least one phase of the multiphase fluid.

19. The method as recited in claim 18, wherein positioning comprises positioning the choke valve and the process line at a subsea location.

20. The method as recited in claim 18, wherein using the sensor comprises monitoring a property of a water phase separated from the multiphase fluid.

* * * * *